United States Patent [19]
Fischer et al.

[11] Patent Number: 5,558,230
[45] Date of Patent: Sep. 24, 1996

[54] DENTAL IMPLANT CONTAINER WITH CAP FOR HOLDING A DENTAL IMPLANT AND HEALING SCREW

[75] Inventors: David V. Fischer, West Jordan, Utah; Riccardo Ilic, Milan, Italy

[73] Assignee: Ultradent Products, South Jordan, Utah

[21] Appl. No.: 474,475

[22] Filed: Jun. 7, 1995

[51] Int. Cl.⁶ .................................................. B65D 85/20
[52] U.S. Cl. ........................ 226/570; 206/63.5; 433/174
[58] Field of Search ................................. 206/63.5, 363, 206/368, 369, 370, 438, 570; 433/173, 174, 201.1

[56] References Cited

U.S. PATENT DOCUMENTS

| | | | |
|---|---|---|---|
| 4,671,410 | 6/1987 | Hansson et al. | 206/438 |
| 4,712,681 | 12/1987 | Branemark et al. | 206/438 |
| 4,763,788 | 8/1988 | Jorneus et al. | 206/438 |
| 4,988,292 | 1/1991 | Rosen | 433/173 |
| 5,312,254 | 5/1994 | Rosenlicht | 206/63.5 |
| 5,368,160 | 11/1994 | Leuschen et al. | 206/63.5 |

FOREIGN PATENT DOCUMENTS 2611484  9/1988  France ........................ 433/201.1

OTHER PUBLICATIONS

Actual Product Sample—device used for storing dental implant and healing screw on sale, or known or used in this country prior to Applicant's filing date.

Primary Examiner—Jimmy G. Foster
Attorney, Agent, or Firm—Workman Nydegger Seeley

[57] ABSTRACT

A container shaped to allow a dental technician to avoid touching or contaminating a dental implant and healing screw stored therein while placement of these at a dental surgical site. The container has a carrier for storing the implant and healing screw. A transparent hood seals the carrier from the ambient. The dental implant is held at an end thereof within the carrier with its longitudinal axis normal to the longitudinal axis of the healing screw in its position in a cavity in the carrier. A tool passage in the carrier provides access to the cavity for a placement tool that is attached to the healing screw in order to remove the same from the carrier. A cylindrical base on the carrier, terminated at opposite ends thereof by radially projecting flanges, provides a gripping surface for the thumb and index finger of a dental technician during removal of the implant and healing screw from the carrier. The flanges serve as a tactilely sensed positioning guide for digitally gripping the carrier while a dental technician removes the transparent hood, implant, and healing screw from the carrier.

21 Claims, 4 Drawing Sheets

DENTAL IMPLANT CONTAINER WITH CAP FOR HOLDING A DENTAL IMPLANT AND HEALING SCREW

THE FIELD OF THE INVENTION

The invention relates to storing and dispensing a dental implant having a healing screw and is more particularly related to a container for holding a dental implant and healing screw.

BACKGROUND OF THE INVENTION

An implant is used to provide support to a patient having a tooth loss, where there is only oral tissues and bone available to support a prosthesis or a restoration intraorally. An implant fixture allows a rigid fixed restoration so as to provide function for a patient. To prepare the mouth of a patient for such a prosthesis or restoration, a geometrical form is created in the jaw bone of a patient specific to the geometry of the implant fixture. Such geometry may be, by way of example, cylindrical or blade-like. Other geometries are also known. The geometry of the preparation is made into the bone or osseous structure of the patient.

After the preparation of the bone or osseous structure, a dental implant is then placed into the preparation in the osseous structure in the jaw bone of the patient using an implant placement instrument affixed to the implant. Then, a healing screw placement instrument is used to place and fixedly attach the healing screw over and into an opening to the inside of the implant. The healing screw caps off the inside of the implant from the mouth of the patient. The healing screw is necessary so that oral tissues of the patient will not grow down or migrate into the inside of the implant.

After the healing screw has been placed with the healing screw placement instrument into the superior end of the implant, sutures are made into the oral mucosa over the access site to begin the healing process. After a period of time, osteointegration functions of the patient cause the bone to grow back into and around the implant so as to provide a stable, non-mobile implant.

Some prior art containers used to store a dental implant and healing screw prior to use are designed to require that a dental technician touch or handle either the dental implant or the healing screw in order to remove the same from the container prior to placement of these into a surgical preparation site in the jaw bone of a patient. Other such containers require a high level of manual adeptness and skill in handling in order to remove them from their containers without touching the same. A high level of manual dexterity required to handle these containers without touching the implant or healing screw increases the likelihood of dropping, touching, or otherwise contacting the implant or healing screw.

When there has been a dropping, touching, or contacting of the implant or healing screw, contaminants will likely be introduced on to the surface of these. Such contaminants, when so introduced, will likely also contaminate the surgical preparation site within the sterile field. A consequence of contamination of the sterile field is that a negative or adverse effect can be had upon the natural healing process of osteointegration of the implant into the surgical site in the jaw bone of the patient. Such contamination can be bacterial or microbial. Contamination can also be caused by oxides from skin, silicone, surgical glove contact, or anything that alters the basic chemical and physical properties of the oxide layer on the implant.

Given the above, it would be an advance in the art to provide a container for an implant and healing screw that can be easily handled by a dental technician to remove the same from the container and place both the implant and the healing screw using placement tools at the surgical site in the jaw bone of the patient without dropping, touching or contacting these with any surface other than that of the placement tools. It would be a further advancement in the relevant art to provide an implant container that affords a dental technician the ability to easily remove an implant and healing screw therefrom with placement instruments without touching either of these, which ease is facilitated in part by relative orientation positions of the healing screw and implant within the container.

SUMMARY AND OBJECTS OF THE INVENTION

It is an object of this invention to provide a container for an implant and healing screw that is easily handled by a dental technician to remove the same from the container and place both the implant and the healing screw using surgical placement tools at the surgical site in the jaw bone of the patient without dropping, touching, or contacting these with any surface other than that of the surgical placement tools.

The objects of this invention are accomplished by a container that orients the longitudinal axis of the implant normal to that of the healing screw, while resiliently holding both of these within the container. The container affords access to placement tools for removal of the implant and healing screw from the container. The access path of the placement tools for removal of the implant and the healing screw are, respectively, substantially normal one to another.

Cavities within the container, which are dimensioned to resiliently hold the implant and healing screw therein, limit the exposed surface area of the implant and healing screw to the ambient. A transparent hood covers both the implant and healing screw while they are stored in the container. A ribbing feature radially projects from the surface of the container to tightly seal the hood over the implant and healing screw, and to guide the removal of the hood from the container so as to avoid contacting the interior surface of the hood with the implant.

The container has a flat bottom so that is may it may be placed standing upright on a flat surface, such as a mobile surgical tray, after the removal of the implant from the container during placement of the same at the surgical site. The flat surface on the container prevent it from rolling around on the mobile surgical tray. One or more flanges radially project from the outside surface of the container to serve as a tactile guide for placing the fingering on the container in a proper grip thereon while removing the implant and healing screw therefrom using placement tools.

The inventive implant container provides only two parts, a carrier and a hood, in order to store the implant and healing screw. The fewer parts, the less manual dexterity required of the dental technician during the implant placement surgical procedure. Further, the design of the inventive implant container requires only moderate manual adeptness and skill to remove the implant and healing screw from the inventive container, which in turn lessens the possibility of dropping or fumbling the implant or healing screw during the surgical placement procedure. The geometry of the inventive implant container provides ease of use so as to reduce the likelihood that the implant or healing screw will be contacted by surgical gloves, skin, or bacterial contamination. Contamination is to be avoided in that it has the potential of affecting the normal healing process of tissue in the surgical preparation made in the bone or osseous structure of the patient. The healing process is important to integrate the implant with the bone of the patient and the oral cavity therein. By lowering the risk of contamination, a better implant container is achieved.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
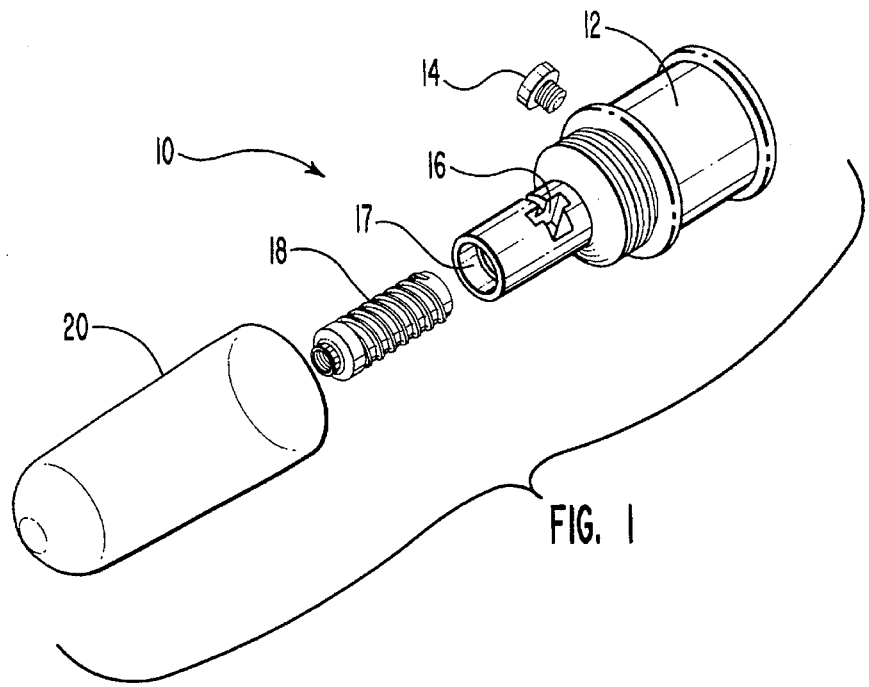
FIG. 1 is an exploded perspective view of the inventive container for an implant and healing cap screw, the container having a carrier with cavities therein for resiliently holding the implant and healing cap screw, and having a transparent hood for sealing over the cavities, implant, and healing cap screw while being resiliently held against a carrier.
Figure 2:
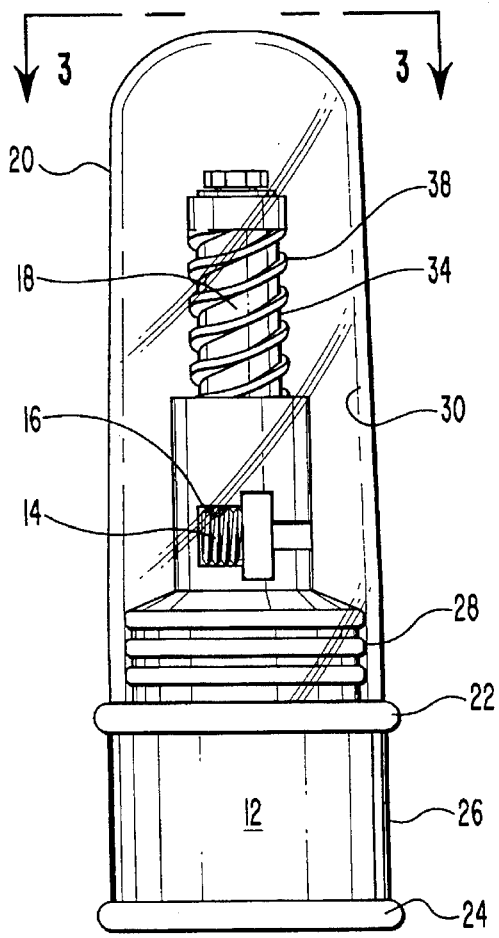
FIG. 2 is a front elevational view of the assembled container of FIG. 1 holding the implant and healing cap screw with the transparent hood in place thereover.
Figure 3:
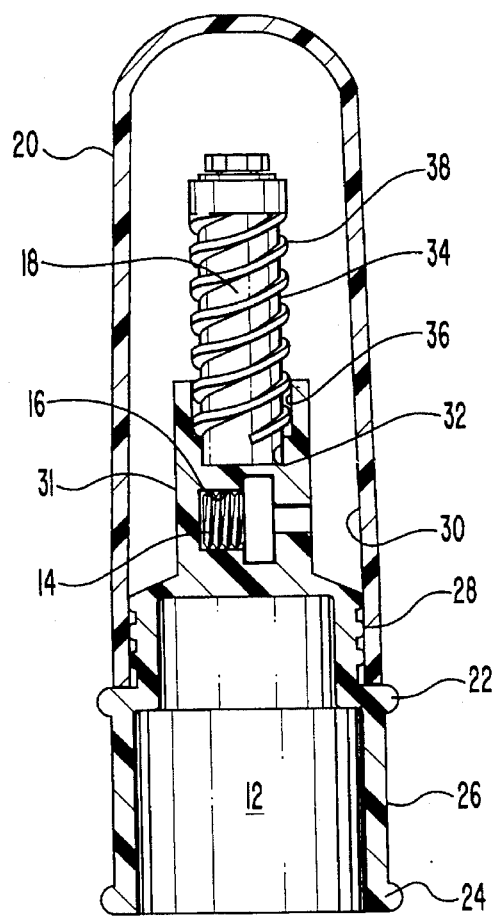
FIG. 3 is a cross sectional view taken along section line 3—3 of FIG. 2 showing the dimensioning of the cavity in the carrier for resiliently holding the implant, and showing the resilient fit of the transparent hood over a ribbing that radially projects from the outer surface of the carrier so as to seal the implant and healing cap screw from the ambient.

A preferred embodiment of the inventive dental implant container with cap for holding a dental implant and a healing cap screw is seen in FIGS. 1–6 as implant container 10. A healing cap screw 14 and a dental implant 18 held by an implant container 10 are seen in FIGS. 1–3. Implant container 10 has a carrier 12 that is made from sterilizable medical grade plastic. The carrier of the inventive implant container has a means for holding a healing screw in a fixed position with the longitudinal axis of the healing screw making an angle with the longitudinal axis of the dental implant. By way of example and illustration of the healing screw holding means, a screw cavity 16 in carrier 12 substantially encloses and retains healing cap screw 14 therein.

The carrier of the inventive implant container also has a means for holding a dental implant in a fixed position. By way of example and illustration of the dental implant holding means, carrier 12 has at the distal end thereof a cavity or receptacle 17 that receives and resiliently holds an end of implant 18 therein.

A hood having a means to seal the dental implant and the healing screw from the ambient is also part of the inventive implant container. By way of example and illustration of the hood and the means for sealing the dental implant and the healing screw from the ambient, a hood 20 circumscribes a plurality of ribs 28, seen in FIG. 2, on the outside surface of carrier 12. Thus, hood 20 is placed over implant 18 onto carrier 12 so as to seal both cavities 16 and 17 from the ambient.

FIGS. 2 and 3 show the assembled view of implant container 10. Carrier 12 has a base 26 having a distal flange 22 and a proximal flange 24 thereon. Base 26 is preferably greater than 0.2 inches, and is more preferably 0.3 inches in length. Distally of base 26 of carrier 12 a ribbing 28 projects radially from the outer surface of carrier 12. Ribbing 28 has an outer diameter that is approximately equal to or greater than an internal surface 30 of hood 20. When hood 20 is placed over ribbing 28 on carrier 12, a friction fit is made between interior surface 30 of hood 12 and ribbing 28 of carrier 12.

A cylindrical projection 31 is situated at a distal end of carrier 12. Cylindrical projection 31 has receptacle 17 therein as seen in FIG. 1. Receptacle 17 has a first cylindrical cavity 32 that has a smaller inner diameter than a second cylindrical cavity 36 also in receptacle 17. Implant 18 has an outer surface 34 with a plurality of cutting threads 38 extending from outer surface 34 of implant 18. Outer surface 18 has an outer diameter that is approximately equal to the inner diameter of first cylindrical cavity 32 of receptacle 17. Cutting threads 38 have an approximate outer diameter that is preferably slightly less than second cylindrical cavity 36 of receptacle 17. The reason for such preference of diametrical difference is that cutting threads 38 should be dimensioned so as to avoid cutting or shaving the material on the surface of second cylindrical cavity 36 and receptacle 17. First cylindrical cavity 32, which is not necessarily an abrasive surface, will not be subject to the same problem of removing material from first cylindrical cavity 32 of receptacle 17 as is experienced by the sharp cutting edges of cutting threads 38. Thus, outer surface 34 of implant 18 is not in danger of removing the material on the surface of first cylindrical cavity 32 of receptacle 17.

Figure 4:
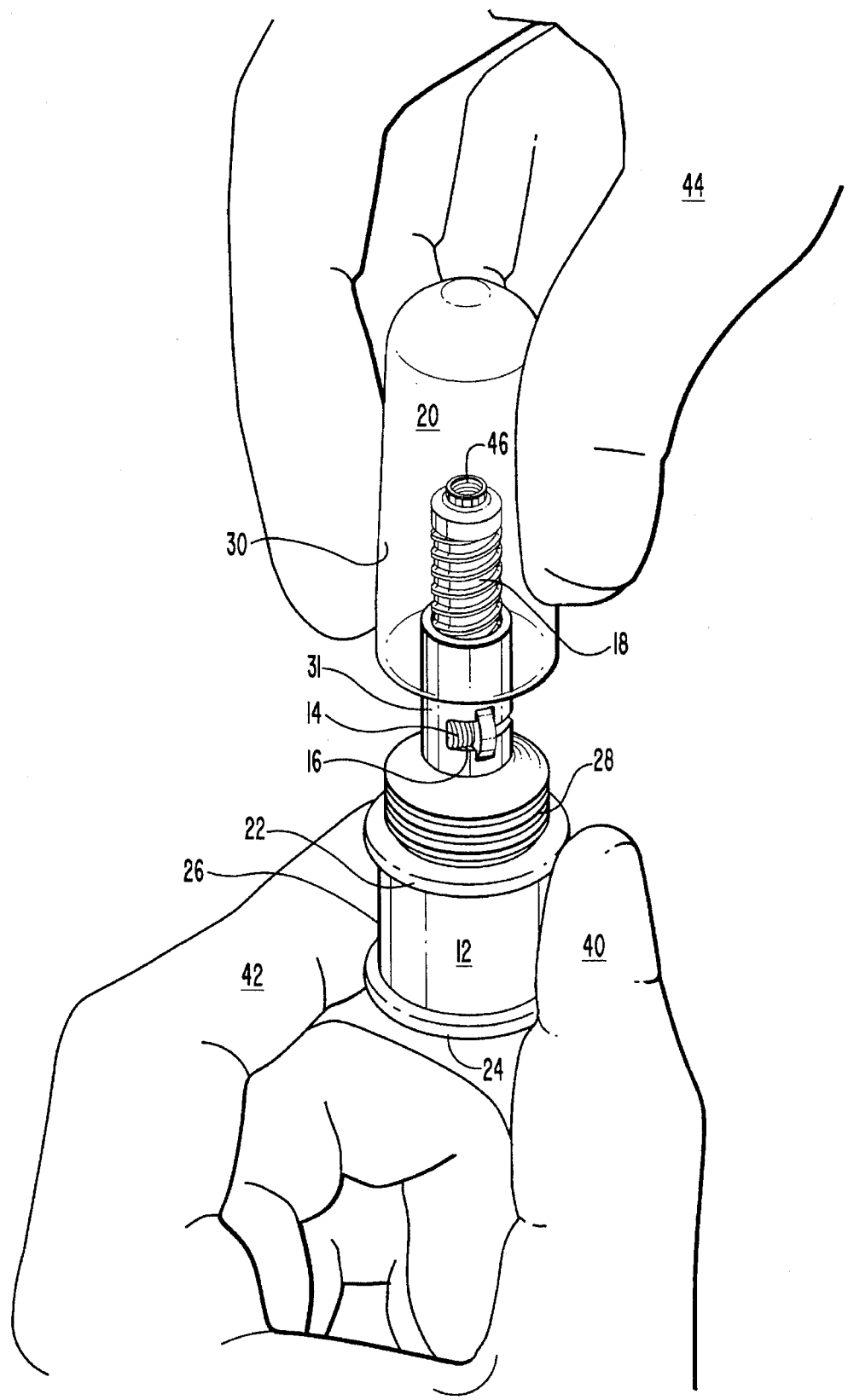
FIG. 4 shows the container of FIG. 1 with a hand of a dental technician removing the transparent hood from over the ribbing on the carrier past a distal end of the implant without contacting the inner surface of the hood with the implant, while the other hand of the dental technician grips the carrier upon a base of the carrier situated between two radially projecting flanges that provide a tactile guide for the fingers of the hand that grip the carrier and prevent the fingers of the dental technician from slipping during the removal of the hood.

FIG. 4 show the placement of an index finger 42 and a thumb 40 in between distal end flange 22 and proximal end flange 24, and on base 26 of carrier 12. At least distal flange 22 should be present on various embodiments of base 26 of carrier 12 so that index finger 42 and thumb 40 can be properly placed by tacitly feeling base 26 of carrier 12. Thus, the presence of at least one of flanges 22, 24 enables a user to make proper finger placement on base 26, and properly hold carrier 12 during use.

FIG. 4 show a hand 44 of a user moving hood 20 over and past ribbing 28 of carrier 12. Ribbing 28 extends from distal flange 22 sufficiently so that it is unlikely that internal surface 30 of hood 20 will come in contact with implant 18. Thus, the geometry of ribbing 28 guides hand 44 there over and past cylindrical projection 31, and over implant 18 so that hood 20 clears implant 18 without touching the same.

Figure 5:
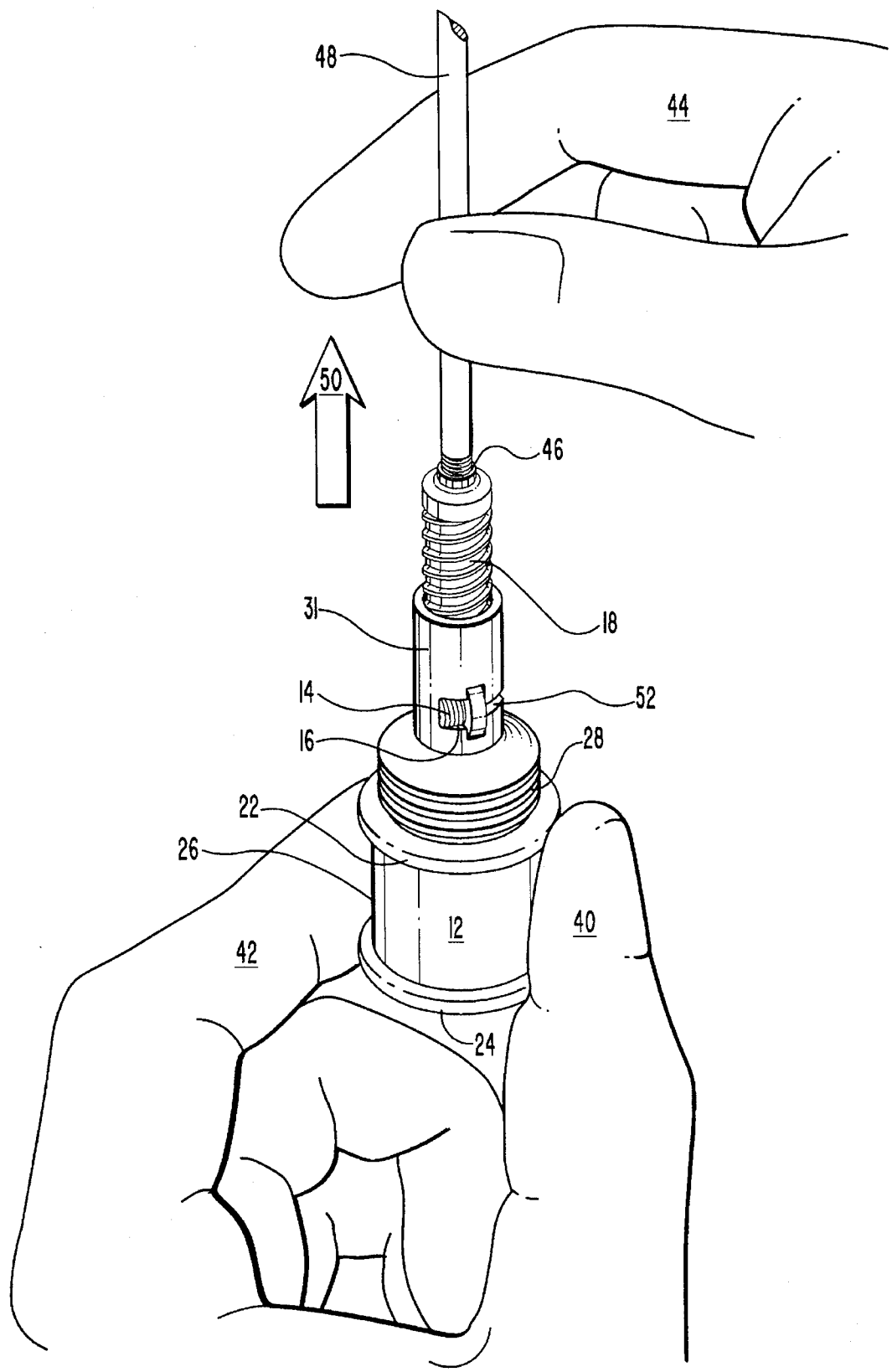
FIG. 5 shows the container of FIG. 1 with the hand of the dental technician placement tool that has been fixably attached to a superior end of the implant and is being used to remove the resiliently held implant from its cavity in the carrier, and shows the fingers of the hand of the dental technician, placed as was shown in FIG. 4, so as to prevent the same from slipping during the removal of the resiliently held implant from its cavity in the carrier.

Once hood 20 of implant container 10 is removed, implant 18 is exposed so that it may accessed by an implant placement instrument 48, as is shown in FIG. 5. The placement geometry at the end of implant placement tool 48 is such as to conform with the placement geometry at a superior end 46 of implant 18 so as to form a attachment means therebetween. Implant placement instrument 48 may have a male external threading thereon which is correspondingly threaded into internal female threading at superior end 46 of implant 18. The mutual threading together of implant placement instrument 48 and implant 18 serves to form a connection there between so that implant 18 may be removed from carrier 12 once such connection is made. When the connection between implant placement instrument 48 and implant 18 is made, implant 18 is removed from carrier 12 and is taken directly to the surgical site for installation into the oral cavity prepared in the bone or osseous structure of the patient. During the process of removing the implant from the implant container, the dental technician does not touch implant 18 so that all compatibility is preserved between the oral cavity in the bone or osseous structure of the patient and implant 18.

In FIG. 5, implant 18 is in the process of being removed from carrier 12. Hand 44 is holding implant instrument 48 that has been inserted into superior end 46 of implant 18. Implant instrument 48 has at end thereof means for attaching to superior end 46 of implant 18, such that a connection can be fixed between implant instrument 48 and implant 18. Upon such connection being made between implant instrument 48 and implant 18, hand 44 exerts a force in the direction indicated by an arrow 50 so as to remove implant 18 from receptacle 17 seen in FIG. 1. As mentioned above, the removal of implant 18 from receptacle 17 with implant instrument 48 is such that material found on the inside surface of receptacle 17 is not scraped off or otherwise removed by such removal due to the geometry of the inside surfaces of receptacle 17.

Figure 6:
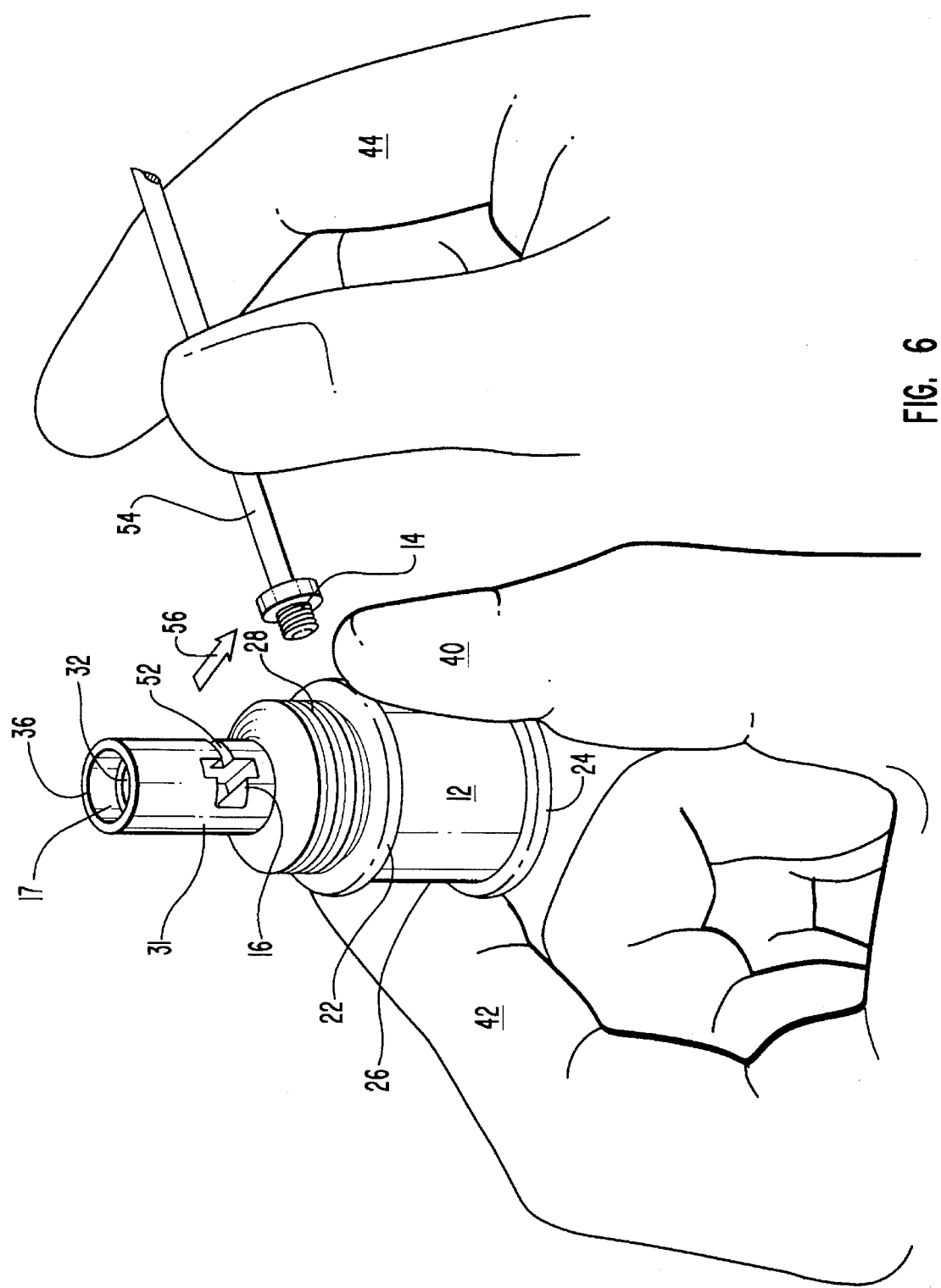
FIG. 6 shows the container of FIG. 1 with the hand of the dental technician gripping a placement tool that has been fixably attached to a superior end of the healing cap screw and is being used to remove the resiliently held healing cap screw from its cavity in the carrier, and shows the fingers of the hand of the dental technician, placed as was shown in FIG. 4, so as to prevent the same from slipping during the removal of the resiliently held healing cap screw from its cavity in the carrier.

FIG. 6 shows carrier 12 with implant 18 removed from receptacle 17. Also shown in FIG. 6 is the result of a process for removing healing cap screw 14 from cap screw cavity 16 using healing cap screw placement instrument 54. Healing cap screw 14 has an external threading thereon which is threaded into superior end 46 of implant 18 after implant 18 has been placed into the oral cavity of the bone of the patient. Healing cap screw 14 caps off the internal threads of implant 18 in superior end 46 so as to seal the same and prevent the growth of oral tissues of the patient into or migrating into the internal threading at superior end 46 of implant 18. The geometry of healing cap screw 14 conforms to the geometry of a healing screw placement instrument 54 may be hexagonal, slotted or other geometry such as to form an attachment means between healing screw placement instrument 54 and the superior end of healing cap screw 14.

To effect the removal of healing cap screw 14 from cap screw cavity 16, hand 44 grasps healing cap screw placement instrument 54 and inserts the same into a tool passage 52 so that an end of healing cap screw placement instrument 54 can be inserted into and connected with a superior end of healing cap screw 14. By way of example, and not by way of limitation, the end of healing cap screw placement instrument 54 may have an allen wrench geometry that correspondingly conforms to the superior end of healing cap screw 14 so that a fixed attachment can be made therebetween sufficient to enable removal of healing cap screw 14 from its resiliently held position within cap screw cavity 16 of carrier 12.

After healing screw placement instrument 54 has been fixedly connected and attached to healing cap screw 14, hand 44 exerts a force upon healing cap screw placement 54 in the direction of an arrow 56 seen in FIG. 6. Carrier 12 is preferably made of resilient material such that healing cap screw 14 is resiliently pried out of cap screw cavity 16, while healing cap screw placement 52 slides through tool passage 54 in the direction indicated by arrow 56. After such removal of healing cap screw 14 from carrier 12, healing cap screw placement instrument 54 is then used to place healing cap screw 14 into superior end 46 of implant 18, which implant 18 is implanted into a surgical preparation site in the jaw bone of a patient.

The present inventive implant container can be geometrically shaped so as to hold an implant having either a cutting screw fit or a press fit. Additionally, such an implant may be plasma coated so as to provide a mechanical relief surface thereon. Such a plasma coating may be a metal oxide, or may be a hydroxy appetite crystalline material applied to the surface of a titanium alloy implant. Such an hydroxy appetite crystalline material can be a coating on either a press fit implant or a cutting thread implant geometry, which alternative geometries are contemplated within the scope of the present invention.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A container for a dental implant having a first longitudinal axis and a healing screw having a head and a shaft with a second longitudinal axis that extends centrally of the shaft comprising:

a carrier having means for holding the dental implant in a fixed position and having means for holding the healing screw in a fixed position with the second longitudinal axis of the healing screw making a transverse angle with the first longitudinal axis of the dental implant; and a hood in contact with the carrier having means to seal the dental implant and the healing screw from the ambient.

2. The container as defined in claim 1, wherein said carrier has a proximal end and an opposite distal end comprising a cylindrical projection with a first cavity for receiving an end of the dental implant, and a second cavity therein for substantially enclosing and retaining the healing screw in said fixed position, the cylindrical projection having an outside surface and a tool passage extending from the outside surface to the second cavity, the tool passage providing access for removal of said healing screw from said second cavity.

3. The container as defined in claim 2, wherein the carrier means comprises an outside surface, a portion of which has a plurality of ribs radially encircling and extending therefrom, and a flange extending therefrom distal of said plurality of ribs.

4. The container as defined in claim 3, wherein the hood is in contact with the flange and circumscribes the plurality of ribs, whereby the hood seals both the first and second cavities from the ambient.

5. The container as defined in claim 4, wherein a second distal flange extends from the distal end of the carrier to a flat surface.

6. The container as defined in claim 2, wherein the hood is transparent to allow a user visibility to the healing screw and the dental implant.

7. The container as defined in claim 2, wherein the first cavity resiliently holds said dental implant in said fixed position.

8. The container as defined in claim 2, wherein the second cavity resiliently holds said healing screw in said fixed position.

9. The container as defined in claim 2, wherein said portion having said ribs and the proximal end are both cylindrical, and wherein the proximal end has a larger cross-sectional diameter than that of said portion having said ribs, and wherein said portion in turn has a larger cross-sectional diameter than that of the cylindrical projection of the distal end.

10. A container for a dental implant having a first longitudinal axis and a healing screw having a head and a shaft with a second longitudinal axis that extends centrally of the shaft, comprising:

a carrier having a proximal end and an opposite distal end, the distal end comprising means for holding the dental implant in a fixed position, and means for holding the healing screw in a fixed position with the second longitudinal axis of the healing screw perpendicular to the first longitudinal axis of the dental implant; and a hood in contact with the carrier and having means to seal the dental implant and the healing screw from the ambient.

11. The container as defined in claim 10, wherein said distal end comprises a cylindrical projection comprising a first cavity for resiliently holding therein an end of the dental implant, and a second cavity therein for substantially enclosing and resiliently holding therein the healing screw, the cylindrical projection having an outside surface and a tool passage extending from the outside surface to the second cavity, the tool passage having a longitudinal axis in common with the second longitudinal axis of the healing screw.

12. The container as defined in claim 11, wherein the carrier means comprises an outside surface, a portion of which has a plurality of ribs radially encircling and extending therefrom, and a flange extending therefrom distal of said plurality of ribs.

13. The container as defined in claim 12, wherein the hood is in contact with the flange and circumscribes the plurality of ribs, whereby the hood seals both the first and second cavities from the ambient.

14. The container as defined in claim 13, wherein a second distal flange extends from the distal end of the carrier to a flat surface.

15. The container as defined in claim 11, wherein the hood is transparent to allow a user visibility to the healing screw and the dental implant.

16. The container as defined in claim 11, wherein said portion having said ribs and the proximal end are both cylindrical, and wherein the proximal end has a larger cross-sectional diameter than that of said portion having said ribs, and wherein said portion in turn has a larger cross-sectional diameter than that of the cylindrical projection of the distal end.

17. A container for a dental implant having a first longitudinal axis and a healing screw having a head and a shaft with a second longitudinal axis that extends centrally of the shaft, comprising:

a carrier having a cylindrical proximate end opposite a cylindrical distal end and a cylindrical portion therebetween, the proximal end having a larger cross-sectional diameter than that of said portion, and said portion having a larger cross-sectional diameter than that of the distal end, the distal end having a first cavity for receiving an end of the dental implant, and a second cavity therein for substantially enclosing and retaining the healing screw with the second longitudinal axis of the healing screw perpendicular to the first longitudinal axis of the implant, said distal end having a tool passage extending from an outside surface thereof to the second cavity, the tool passage having a longitudinal axis in common with to the second longitudinal axis of the healing screw, and said portion between the distal and proximal ends having a plurality of ribs radially encircling and extending therefrom and having a first flange extending therefrom distal of the plurality of ribs, a second distal flange extending from the distal end of the carrier; and a hood in contact with the first flange and circumscribing the plurality of ribs, whereby the hood seals both cavities from the ambient.

18. The container as defined in claim 17, wherein the hood is transparent to allow a user visibility to the healing screw and the dental implant.

19. The container as defined in claim 17, wherein the first cavity resiliently holds said dental implant in said fixed position.

20. The container as defined in claim 17, wherein the second cavity resiliently holds said healing screw in said fixed position.

21. A container for a dental implant and a healing screw comprising:

a carrier means comprising a projecting portion with an opening in an end of the projecting portion for holding the dental implant in a fixed position, and said projecting portion further comprising a circumferential sidewall with an opening for holding the healing screw in a fixed position therein; and a hood adapted to contact the carrier means so as to seal the dental implant and the healing screw from the ambient.

* * * * *